(12) United States Patent
Smith et al.

(10) Patent No.: US 9,568,621 B2
(45) Date of Patent: Feb. 14, 2017

(54) IMAGING SYSTEM AND METHODS OF MANUFACTURING AND USING THE SAME

(71) Applicants: Joseph T. Smith, Tempe, AZ (US); John Stowell, Tempe, AZ (US)

(72) Inventors: Joseph T. Smith, Tempe, AZ (US); John Stowell, Tempe, AZ (US)

(73) Assignee: ARIZONA BOARD OF REGENTS, A BODY CORPORATE OF THE STATE OF ARIZONA, ACTING FOR AND ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 79 days.

(21) Appl. No.: 14/569,381

(22) Filed: Dec. 12, 2014

(65) Prior Publication Data

US 2015/0139397 A1 May 21, 2015

Related U.S. Application Data

(63) Continuation of application No. PCT/US2013/045334, filed on Jun. 12, 2013.
(Continued)

(51) Int. Cl.
*G01T 1/29* (2006.01)
*H04N 5/32* (2006.01)
(Continued)

(52) U.S. Cl.
CPC ............ *G01T 1/2928* (2013.01); *G01N 23/04* (2013.01); *H01L 27/1469* (2013.01);
(Continued)

(58) Field of Classification Search
CPC ....... A61B 6/4233; A61B 6/4266; H04N 5/32; G01T 1/2928
(Continued)

(56) References Cited

U.S. PATENT DOCUMENTS 5,962,856 A * 10/1999 Zhao ................. H01L 27/14665
250/370.02
6,005,908 A * 12/1999 Oppelt .................. G01T 1/2985
378/11
(Continued)

FOREIGN PATENT DOCUMENTS

| JP | 2004-309868 | 11/2004 |
|---|---|---|
| KR | 10-0835892 | 6/2008 |
| WO | WO 2012/021196 A2 * | 2/2012 |

OTHER PUBLICATIONS

International Search Report and Written Opinion for PCT/US2013/04334 dated Jan. 14, 2014.

*Primary Examiner* — Allen C. Ho

(74) *Attorney, Agent, or Firm* — Bryan Cave LLP

(57) ABSTRACT

Some embodiments include an imaging system. The image sensor array includes multiple image sensor sheets configured in an array grid. Each image sensor sheet of the multiple image sensor sheets can include a flexible substrate layer, and the flexible substrate layer can include a first flexible substrate side and a second flexible substrate side opposite the first flexible substrate side. Meanwhile, each image sensor sheet of the multiple sensor sheets can include multiple image sensors over the first flexible substrate side, the multiple image sensors can include multiple flat panel image detectors configured in a sheet grid, and the image sensor array can include an approximately constant pixel pitch. Other embodiments of related systems and methods are also disclosed.

13 Claims, 11 Drawing Sheets

Related U.S. Application Data

(60) Provisional application No. 61/658,829, filed on Jun. 12, 2012.

(51) Int. Cl.
*H01L 27/146* (2006.01)
*G01N 23/04* (2006.01)

(52) U.S. Cl.
CPC .. *H01L 27/14658* (2013.01); *H01L 27/14685* (2013.01); *H04N 5/32* (2013.01)

(58) Field of Classification Search
USPC .............................. 378/19, 98.8; 250/370.09
See application file for complete search history.

(56) References Cited

U.S. PATENT DOCUMENTS

| | | | | |
|---|---|---|---|---|
| 6,274,225 B1 * | 8/2001 | Miyake | ................ | H05K 1/0326 174/254 |
| 6,426,991 B1 * | 7/2002 | Mattson | ................ | A61B 6/032 378/19 |
| 6,453,008 B1 * | 9/2002 | Sakaguchi | ............... | H04N 5/32 250/370.09 |
| 6,510,195 B1 * | 1/2003 | Chappo | ................. | G01T 1/2018 250/208.1 |
| 6,823,039 B2 * | 11/2004 | Hoheisel | ................ | A61B 6/032 378/19 |
| 6,856,670 B2 * | 2/2005 | Hoheisel | ........... | H01L 27/14658 250/370.09 |
| 6,990,176 B2 * | 1/2006 | Sherman | ................ | A61B 6/032 250/370.09 |
| 7,117,588 B2 * | 10/2006 | Vafi | ................... | H01L 27/14658 250/208.1 |
| 7,122,802 B2 * | 10/2006 | Petrick | .................... | H04N 5/32 250/370.01 |
| 7,235,790 B2 * | 6/2007 | Hoge | .................... | G01T 1/1648 250/370.09 |
| 7,260,180 B2 * | 8/2007 | Wieczorek | ........ | H01L 27/14676 257/E27.146 |
| 7,289,336 B2 * | 10/2007 | Burdick, Jr. | ........... | H05K 1/147 257/428 |
| 7,426,259 B2 * | 9/2008 | Weisfield | ................. | H04N 5/32 250/370.09 |
| 7,435,965 B2 * | 10/2008 | Fuchs | ................... | G01T 1/2018 250/367 |
| 7,495,228 B1 * | 2/2009 | Albagli | ............. | H01L 27/14663 250/370.09 |
| 7,742,090 B2 * | 6/2010 | Street | ................ | H01L 27/14601 348/264 |
| 7,787,592 B2 * | 8/2010 | Okamura | ................ | A61B 6/032 250/370.09 |
| 7,810,997 B2 * | 10/2010 | Okamura | ................ | A61B 6/00 378/207 |
| 7,817,204 B2 * | 10/2010 | Minamio | ............. | H04N 5/2253 348/262 |
| 7,855,369 B2 * | 12/2010 | Takahashi | ................. | G01T 1/24 250/370.01 |
| 8,076,743 B2 * | 12/2011 | Choi | .................... | H01L 27/14601 257/432 |
| 8,324,553 B2 * | 12/2012 | Lee | ................... | H01L 27/14634 250/208.1 |
| 8,431,902 B2 * | 4/2013 | Nakatsugawa | ...... | A61B 6/4208 250/361 R |
| 8,586,934 B2 * | 11/2013 | Nakatsugawa | ....... | G01T 1/2985 250/363.02 |
| 8,992,712 B2 * | 3/2015 | Loy | ..................... | H01L 21/2007 156/247 |
| 8,999,778 B2 * | 4/2015 | O'Rourke | ........... | H01L 21/6835 257/59 |
| 9,158,010 B2 * | 10/2015 | Osawa | .................... | G01T 1/202 |
| 2004/0201888 A1 * | 10/2004 | Hagita | ............... | G02B 27/2228 359/462 |
| 2008/0117324 A1 | 5/2008 | Minamio et al. | | |
| 2008/0151089 A1 | 6/2008 | Street et al. | | |
| 2010/0164038 A1 | 7/2010 | Choi | | |

\* cited by examiner

IMAGING SYSTEM AND METHODS OF MANUFACTURING AND USING THE SAME

CROSS-REFERENCE TO RELATED APPLICATIONS

This application is a continuation of International Patent Application No. PCT/US2013/045334, filed Jun. 12, 2013. International Patent Application No. PCT/US2013/045334 claims the benefit of U.S. Provisional Application No. 61/658,829, filed Jun. 12, 2012. International Patent Application No. PCT/US2013/045334 and U.S. Provisional Application No. 61/658,829 each are incorporated herein by reference in their entirety.

STATEMENT REGARDING FEDERALLY SPONSORED RESEARCH OR DEVELOPMENT

This invention was made with government support under W911NF-04-2-0005 awarded by the Army Research Office. The government has certain rights in the invention.

FIELD OF THE INVENTION

This invention relates generally to imaging systems, and relates more particularly to large area digital imaging systems for imaging objects with high resolution, high imaging readout speed, low thermal noise, and low radiation dose and methods of manufacturing and using the same.

DESCRIPTION OF THE BACKGROUND

Conventional systems for digital imaging (e.g., tomography), such as might be used to perform tomosynthesis for a mammogram, typically implement digital x-ray detectors (e.g., flat panel detectors) configured to be rapidly and/or mechanically repositioned about an object (e.g., a person) to capture a series of multiple x-ray images of the object. The series of multiple x-ray images are then electronically recombined to form a composite three dimensional image of the object.

Generally speaking, the rapid and/or mechanical movement of the digital x-ray detectors in conventional systems for digital imaging can limit the precision (e.g., resolution) of the x-ray images provided by conventional systems for digital imaging, such as, for example, due to alignment errors between x-ray images, vibrations, etc. that inherently occur in such conventional systems. Further, where the object being imaged is a person, the person generally holds her breath while the series of multiple x-ray images are being captured to minimize any movement that could reduce the precision of the x-ray images. Even subtle movements, like those resulting from breathing, can substantially reduce the precision of the x-ray images. However, because one can only hold her breath for so long, maximizing the imaging readout speed of imaging systems can be desirable. Meanwhile, because exposure to radiation is generally detrimental to any object, and particularly so when the object is organic, minimizing the total exposure to radiation (e.g., dose) of the object can also be desirable. However, the extent to which the radiation dose can be limited can be constrained by a quantity of electronically generated noise present in imaging systems. Consequently, reducing the quantity of electronically generated noise in imaging systems can also permit for decreased doses of radiation because less energy can be needed to compensate for the reduced quantity of noise in the imaging systems.

Accordingly, a need or potential for benefit exists for a large area digital imaging system that can image objects with high resolution, high imaging readout speed, low thermal electronically generated noise, and low radiation dose, and for methods of manufacturing and using the same.

BRIEF DESCRIPTION OF THE DRAWINGS

To facilitate further description of the embodiments, the following drawings are provided in which.

Figure 1:
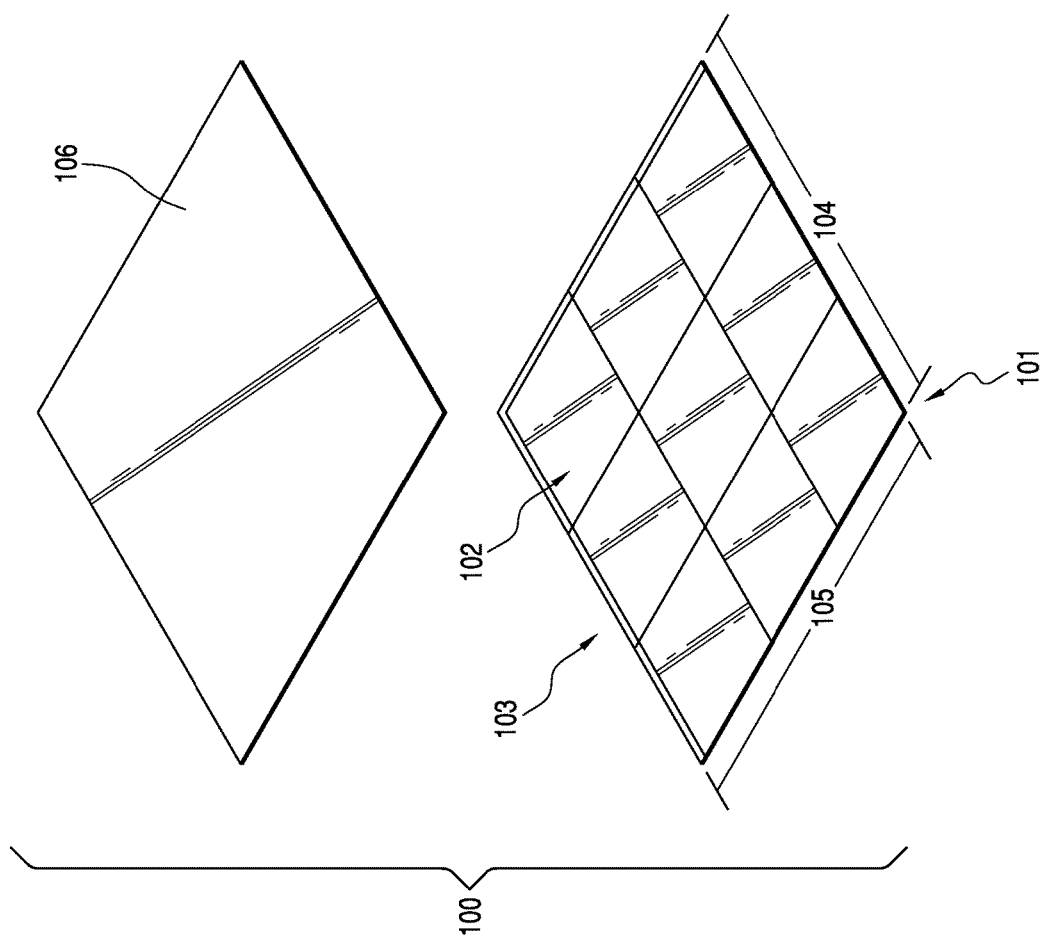
FIG. 1 illustrates an exploded view of an imaging system, according to an embodiment.

For simplicity and clarity of illustration, the drawing figures illustrate the general manner of construction, and descriptions and details of well-known features and techniques may be omitted to avoid unnecessarily obscuring the invention. Additionally, elements in the drawing figures are not necessarily drawn to scale. For example, the dimensions of some of the elements in the figures may be exaggerated relative to other elements to help improve understanding of embodiments of the present invention. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the invention described herein are, for example, capable of operation in other orientations than those illustrated or otherwise described herein.

The terms "couple," "coupled," "couples," "coupling," and the like should be broadly understood and refer to connecting two or more elements or signals, electrically, mechanically and/or otherwise. Two or more electrical elements may be electrically coupled but not be mechanically or otherwise coupled; two or more mechanical elements may be mechanically coupled, but not be electrically or otherwise coupled; two or more electrical elements may be mechanically coupled, but not be electrically or otherwise coupled. Coupling may be for any length of time, e.g., permanent or semi-permanent or only for an instant.

"Electrical coupling" and the like should be broadly understood and include coupling involving any electrical signal, whether a power signal, a data signal, and/or other types or combinations of electrical signals. "Mechanical coupling" and the like should be broadly understood and include mechanical coupling of all types.

The absence of the word "removably," "removable," and the like near the word "coupled," and the like does not mean that the coupling, etc. in question is or is not removable.

DETAILED DESCRIPTION OF EXAMPLES OF EMBODIMENTS

Some embodiments include an imaging system. The imaging system comprises an image sensor array comprising multiple image sensor sheets configured in an array grid. Each image sensor sheet of the multiple image sensor sheets comprises a flexible substrate layer. Meanwhile, the flexible substrate layer comprises a first flexible substrate side and a second flexible substrate side opposite the first flexible substrate side. Further, each image sensor sheet of the multiple sensor sheets comprises multiple image sensors over the first flexible substrate side. The multiple image sensors comprise multiple flat panel image detectors configured in a sheet grid. The image sensor array can comprise an approximately constant pixel pitch.

Various embodiments include a method of manufacturing an imaging system. The method can comprise: manufacturing multiple image sensor sheets; and arranging the multiple image sensor sheets in an image sensor array such that the multiple image sensor sheets form an array grid and such that the image sensor array comprises an approximately constant pixel pitch. Meanwhile, manufacturing the multiple image sensor sheets can comprise: providing a flexible substrate layer of each image sensor sheet of the multiple image sensor sheets, the flexible substrate layer comprising a first flexible substrate side and a second flexible substrate side opposite the first flexible substrate side; and manufacturing multiple image sensors over the first flexible substrate side of each image sensor sheet of the multiple sensor sheets, the multiple image sensors comprising multiple flat panel image detectors configured in a sheet grid.

Further embodiments include a method of imaging an object with an imaging system. The method can comprise: positioning the object between an image sensor array of the imaging system, the image sensor array comprising multiple image sensor sheets configured in an array grid; emitting electromagnetic radiation at the image sensor array and the object; and providing an x-ray representation of the object. Each image sensor sheet of the multiple image sensor sheets comprises a flexible substrate layer. Meanwhile, the flexible substrate layer comprises a first flexible substrate side and a second flexible substrate side opposite the first flexible substrate side. Further, each image sensor sheet of the multiple sensor sheets comprises multiple image sensors over the first flexible substrate side. The multiple image sensors comprise multiple flat panel image detectors configured in a sheet grid. The image sensor array can comprise an approximately constant pixel pitch.

Turning to the drawings, FIG. 1 illustrates an exploded view of imaging system 100, according to an embodiment. Imaging system 100 is merely exemplary and is not limited to the embodiments presented herein. Imaging system 100 can be employed in many different embodiments or examples not specifically depicted or described herein.

Imaging system 100 can be implemented to digitally image (e.g., x-ray image) one or more objects (e.g., one or more persons, one or more body parts and/or organs of the person(s), one or more articles of luggage, etc.), such as, for example, for medical and/or security imaging. Although imaging system 100 can be implemented according to a variety of imaging techniques (e.g., radiography, fluoroscopy, etc.), imaging system 100 can be particularly well suited for tomography, as will be described in greater detail herein. For example, imaging system 100 can be implemented to provide digital tomosynthesis for mammography.

Imaging system 100 comprises image sensor array 101 and scintillator layer 106. Image sensor array 101 comprises multiple image sensor sheets 102. Accordingly, each image sensor sheet of multiple image sensor sheets 102 forms a discrete element of the larger, aggregate image sensor array 101. This relationship of multiple image sensor sheets 102 to image sensor array 101 can provide numerous advantages for imaging system 100 over conventional imaging systems. These advantages are described in further detail herein. In some embodiments, scintillator layer 106 can be omitted.

Multiple image sensor sheets 102 can be configured and/or laid out in array grid 103. Array grid 103 comprises array grid sheet length 104 and array grid sheet width 105. Array grid sheet length 104 can be defined in terms of a number of image sensor sheets of which image sensor array 101 comprises in a longitudinal direction, and array grid sheet width 105 can be defined in terms of a number of image sensor sheets of which image sensor array 101 comprises in a lateral direction. In many embodiments, array grid 103 can comprise a regular Cartesian grid, but in other embodiments, can comprise any other suitable type of grid. For instance, in these other examples, array grid 103 can be asymmetric and/or discontinuous.

Multiple image sensor sheets 102 can comprise as many image sensor sheets as are suitable to implement image sensor array 101 of a desired size. That is, image sensor array 101 can be expanded to any desired size by adding more image sensor sheets thereto. Thus, array grid sheet length 104 and/or array grid sheet width 105 can comprise any suitable number of image sensor sheets. However, in many embodiments, array grid sheet length 104 and/or array grid sheet width 105 can comprise at least three image sensor sheets of multiple image sensor sheets 102. Accordingly, in these examples, multiple image sensor sheets 102 can comprise at least nine image sensor sheets arranged in a regular Cartesian grid. Further, although in these and other embodiments, array grid 103 can comprise a two-dimensional grid, in some embodiments, array grid 103 can comprise a one-dimensional (e.g., linear) grid, such as, for example, where one of array grid sheet length 104 or array grid sheet width 105 comprises one image sensor sheet and the other one of array grid sheet length 104 or array grid sheet width 105 comprises multiple image sensor sheets 102.

Multiple image sensor sheets 102 can be configured to abut and/or partially overlap one another (e.g., at least one or two other image sensor sheets of multiple image sensor sheets 102) when arranged in array grid 103. The lines along which multiple image sensor sheets 102 abut and/or overlap each other can be referred to as seams. In many embodiments, when multiple image sensor sheets 102 are partially overlapping one another (e.g., at least one or two other image sensor sheets of multiple image sensor sheets 102) when arranged in array grid 103, image sensor array 101 can remain approximately planar (e.g., flat) across a surface of an active side of image sensor array 101. Accordingly, the active side of image sensor array 101 can refer to the side of image sensor array comprising the multiple image sensors of each of the image sensor sheets of multiple image sensor sheets 102. Meanwhile, in many examples, a variation in the surface of the active side of image sensor array 101 can be limited to a thickness of one flexible substrate layer (e.g., flexible substrate layer 201 (FIG. 2), flexible substrate layer 301 (FIG. 3), flexible substrate layer 401 (FIG. 4), etc.) of any image sensor sheet of multiple image sensor sheets 102 and/or an extent to which the multiple image sensors (e.g., multiple image sensors 204 (FIG. 2), multiple image sensors 304 (FIG. 3), multiple image sensors 404 (FIG. 4), etc.) project outward from their respective flexible substrate layers. For example, the variation in the surface of the active side of image sensor array 101 can be greater than or equal to approximately 0 micrometers and less than or equal to approximately 200 micrometers.

Image sensor array 101 comprises an approximately constant and/or continuous pixel and/or dot pitch. Further, each image sensor sheet of multiple image sensor sheets 102 can be configured such that the approximately constant and/or continuous pixel pitch remains undisrupted when any image sensor sheet of multiple image sensor sheets 102 partially overlaps one or more other image sensor sheet (e.g., at least one or two other image sensor sheets of multiple image sensor sheets 102) of multiple image sensor sheets 102. Thus, the pixel pitch remains approximately constant even across the seams of image sensor array 101.

In many embodiments, the pixel pitch can be less than or equal to approximately 400 micrometers and greater than or equal to approximately 25 micrometers. In various embodiments, the pixel pitch can be approximately 50 micrometers. Accordingly, the resolution of each image sensor sheet of multiple image sensor sheets 102 can be similar or identical to the pixel pitch of image sensor array 101.

Image sensor array 101 can be flexible such that image sensor array 101 forms one or more substantially continuous curves. In some embodiments, image sensor array 101 can be sufficiently flexible to curve smoothly across image sensor array 101. In other embodiments, image sensor array 101 can be polygonal in order to approximate a desired curvature of image sensor array 101. By adding additional image sensor sheets to image sensor array 101, it is possible to more closely approximately the desired curvature of image sensor array 101.

Each image sensor sheet of multiple image sensor sheets 102 can be coupled (i.e., mechanically) to at least one other image sensor sheet of multiple image sensor sheets 102, such as, for example, by an adhesive material and/or an adhesive tape. In these embodiments, the adhesive material and/or the adhesive tape can be optically transparent. In many examples, some image sensor sheets of multiple image sensor sheets 102 can be coupled to multiple (e.g., two, three, or four) other image sensor sheets of multiple image sensor sheets 102. Coupling multiple image sensor sheets 102 together can help to hold multiple image sensor sheets 102 together as image sensor array 101. In other embodiments, multiple image sensor sheets 102 are not coupled to each other.

Each image sensor sheet of multiple image sensor sheets 102 can be modular with any other image sensor sheets of multiple image sensor sheets 102. That is, each image sensor sheet of multiple image sensor sheets 102 can be the same such that any image sensor sheet of multiple image sensor sheets 102 can be interchanged with any other image sensor sheet of multiple image sensor sheets 102.

Figure 2:
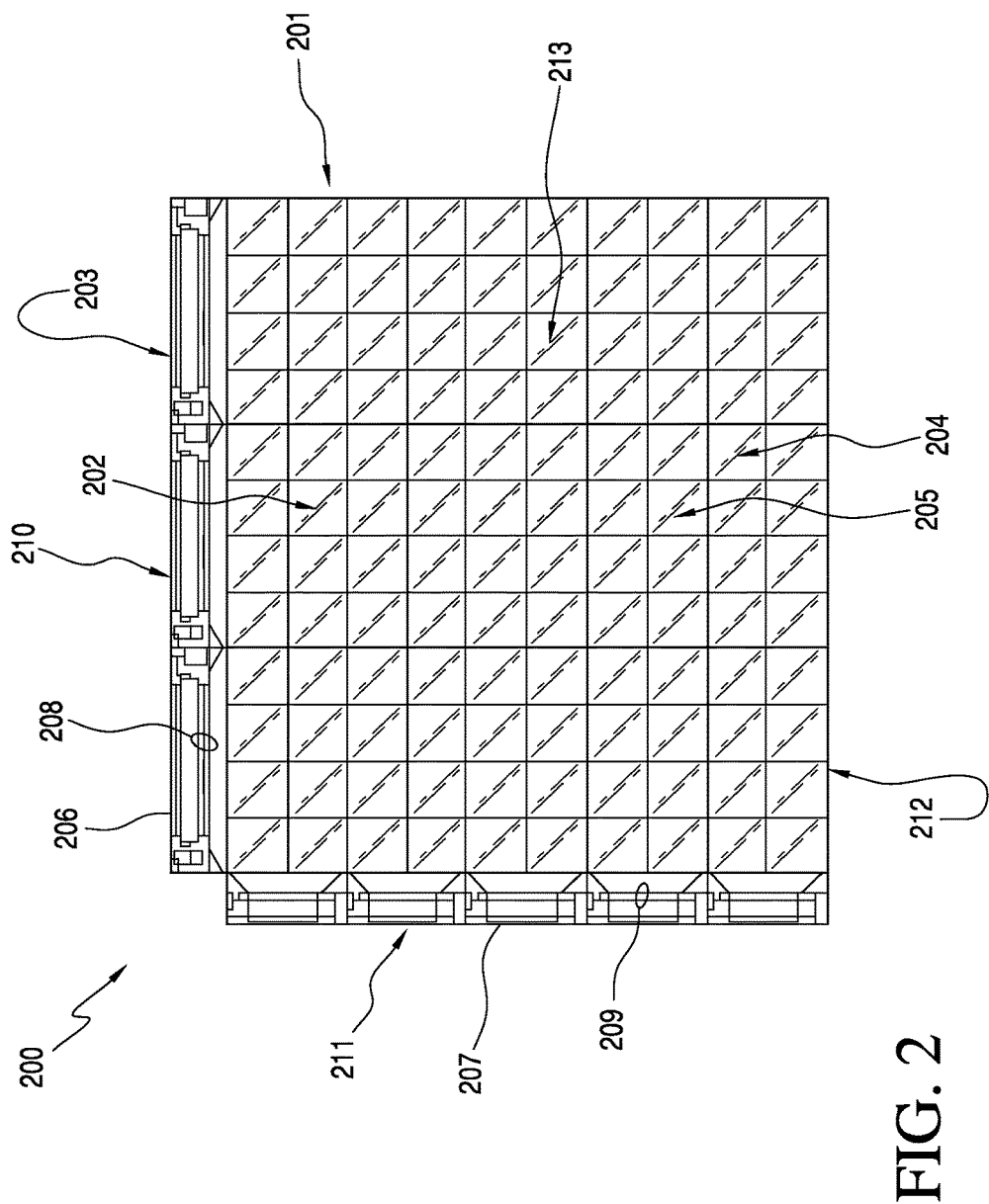
FIG. 2 illustrates a top view of an exemplary image sensor sheet, according to the embodiment of FIG. 1.

Turning now to the next drawing, FIG. 2 illustrates a top view of an exemplary image sensor sheet 200, according to the embodiment of FIG. 1. Each image sensor sheet 200 of multiple image sensor sheets 102 can be similar or identical to image sensor sheet 200.

Image sensor sheet 200 comprises flexible substrate layer 201, multiple image sensors 204, first image sensor sheet edge 206, second image sensor sheet edge 207, multiple row lines 208, and multiple data lines 209. Further, image sensor sheet 200 can comprise one or more row tape automated bond connector(s) 210 and one or more data tape automated bond connector(s) 211. In some embodiments, image sensor sheet 200 can comprise flexible carrier layer 212. Flexible substrate layer 201 comprises first flexible substrate side 202 and second flexible substrate side 203. Second flexible substrate side 203 can be opposite first flexible substrate side 202. Further, multiple image sensors 204 can comprise multiple flat panel image detectors 205.

Flexible substrate layer 201 is flexible. That is, flexible substrate layer 201 can comprise a free-standing substrate that comprises a flexible material which readily adapts its shape. For example, the flexible material can comprise polyethylene naphthalate (PEN), polyethylene terephthalate (PET), polyethersulfone (PES), polyimide, polycarbonate, cyclic olefin copolymer, and/or liquid crystal polymer. An exemplary polyimide flexible material can be Kapton polyimide film as manufactured by E. I. du Pont de Nemours and Company of Wilmington, Del. Flexible substrate layer 201 can comprise a flexible substrate width (e.g., approximately 102 millimeters to approximately 350 millimeters), length (e.g., approximately 102 millimeters to approximately 450 millimeters), and thickness (e.g., greater than or equal to approximately 50 micrometers and less than or equal to approximately 200 micrometers). Although exemplary flexible substrate widths, lengths, and/or thicknesses are provided, the flexible substrate width, length, and/or thickness of flexible substrate layer 201 can be any suitable flexible substrate width, length, and/or thickness, provided flexible substrate layer 201 remains suitably flexible to permit flexible substrate layer 201 to readily adapt its shape. Further, flexible substrate layer 201 can be optically transparent.

Flexible carrier layer 212 is flexible. That is, flexible carrier layer 212 can comprise a free-standing carrier that comprises a flexible material which readily adapts its shape. For example, the flexible material can comprise plastic, carbon fiber, aluminum, and/or fiberglass. In many embodiments, flexible carrier layer 212 can be more rigid than flexible substrate layer 201. At least part of flexible carrier layer 212 can be coupled to flexible substrate layer 201, such as, for example, at second flexible substrate layer 203. In some embodiments, flexible carrier layer 212 and flexible substrate layer 201 can be coupled together by an adhesive material. Flexible carrier layer 212 can be configured to support flexible substrate layer 201, and/or can be implemented for fabrication of image sensor sheet 200. In some embodiments, flexible carrier layer 212 can be omitted. In other embodiments, flexible carrier layer 212 can be decoupled and removed from flexible substrate layer 201 after fabrication of image sensor sheet 200. In some embodiments, flexible carrier layer 212 can be integral with one or more other flexible carrier layers of the image sensor sheets of multiple image sensor sheets 102 (FIG. 1). In other embodiments, each flexible carrier layer 212 can be separate from one or more other flexible carrier layers of the image sensor sheets of multiple image sensor sheets 102 (FIG. 1). In some embodiments, flexible carrier layer 212 can be referred to as a base plate. Flexible substrate layer 201 and flexible carrier layer 212 can be coupled to and/or decoupled from each other according to any suitable coupling/decoupling techniques.

Multiple image sensors 204 (e.g., multiple flat panel image detectors 205) can be located over first flexible substrate side 202. In many embodiments, multiple image sensors 204 can be formed over first flexible substrate side 202 according to any suitable semiconductor manufacturing techniques. U.S. patent application Ser. No. 13/298,451, filed on Nov. 17, 2011 and which issued as U.S. Pat. No. 8,999,778, describes various embodiments of semiconductor manufacturing techniques suitable for forming multiple image sensors 204 over first flexible substrate side 202, and exemplary methods of decoupling and removing flexible carrier layer 212 from flexible substrate layer 201, as described above. Accordingly, U.S. Pat. No. 8,999,778 is incorporated herein by reference in its entirety. Further, International Patent Application Publication Serial Number WO2012/021196, filed May 19, 2011, also describes various embodiments of semiconductor manufacturing techniques suitable for forming multiple image sensors 204 over first flexible substrate side 202, and exemplary methods of decoupling and removing flexible carrier layer 212 from flexible substrate layer 201, as described above. International Patent Application Publication Serial Number WO2012/021196 corresponds to U.S. patent application Ser. No. 13/683,950, filed on Nov. 21, 2012 and which issued as U.S. Pat. No. 8,992,712. Accordingly, U.S. Pat. No. 8,992,712 is incorporated herein by reference in its entirety.

Figure 12:
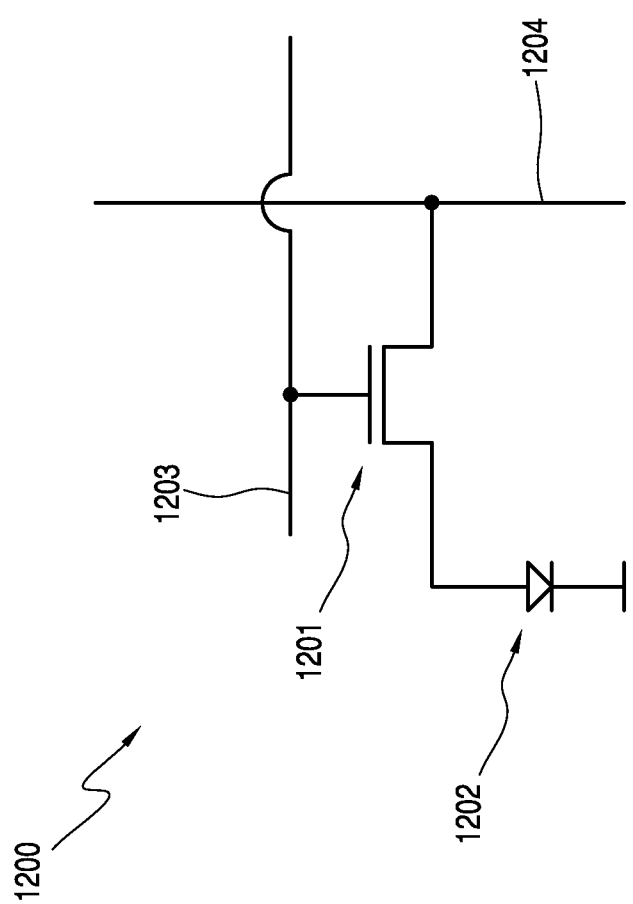
FIG. 12 illustrates an exemplary passive pixel sensor circuit, according to the embodiment of FIG. 1.

In many specific embodiments, each flat panel image detector of multiple flat panel image detectors 205 can comprise an active matrix thin film transistor and an inorganic photodiode (e.g., an amorphous silicon PIN photodiode) and/or an organic photodiode electrically coupled to the active matrix transistor. Meanwhile, each image sensor of multiple image sensors 204 (e.g., multiple flat panel image detectors 205) can be coupled to one row line of multiple row lines 208 and one data line of multiple data lines 209, such as, for example, at the active matrix thin film transistor of each flat panel image detector. In many embodiments, the active matrix thin film transistor and corresponding photodiode can be part of and/or provide a passive pixel (e.g., x-ray) sensor circuit. Further, each flat panel image detector of multiple flat panel image detectors 205 can comprise any other suitable passive pixel circuit. Further still, multiple image sensors 204 can comprise any other suitable continuous thin film imaging active matrix pixel array. FIG. 12 illustrates an exemplary passive pixel sensor circuit 1200 comprising thin film transistor 1201 and photodiode 1202 where thin film transistor 1201 is coupled with photodiode 1202, row line 1203, and data line 1204, according to the embodiment of FIG. 1. Row line 1203 can be similar or identical to one of multiple row lines 208 (FIG. 2), and data line 1204 can be similar or identical to one of multiple data lines 209 (FIG. 2).

Meanwhile, multiple image sensors 204 (e.g., multiple flat panel image detectors 205) can be configured and/or laid out in sheet grid 213 such that sheet grid 213 comprises one or more rows and one or more columns of the image sensors of multiple image sensors 204. Similar to array grid 103 (FIG. 1), in many embodiments, sheet grid 213 can comprise a regular Cartesian grid, but in other embodiments, can comprise any other suitable type of grid. For instance, in these other examples, sheet grid 213 can be asymmetric and/or discontinuous. Accordingly, each of the image sensors in each row of sheet grid 213 can be coupled to the same row line of multiple row lines 208 and each of the image sensors in each column of sheet grid 213 can be coupled to the same data line of multiple data lines 209. Further, as will be described in further detail below, multiple image sensors 204 (e.g., multiple flat panel image detectors 205) can be operated according to an active matrix addressing scheme to implement the imaging functionality of imaging system 100 (FIG. 1).

In many embodiments, multiple row lines 208 can be tape automated bonded at one end of multiple row lines 208 to provide row tape automated bond connector(s) 210, and multiple data lines 209 can be tape automated bonded at one end of multiple data lines 209 to provide data tape automated bond connector(s) 211. Further, row tape automated bond connector(s) 210 can be coupled with an integrated circuit (e.g., a row driver) that is mounted on flex (i.e., chip on flex) and coupled to a signal interface printed circuit board that permits activation/control of multiple row lines 208 of image sensor sheet 200. Meanwhile, data tape automated bond connector(s) 211 can be coupled to the same or another integrated circuit (e.g., a data line driver) that is mounted on flex (i.e., chip on flex) and coupled to the same or another printed circuit board that permits collection of image data from multiple data lines 209 image sensor sheet 200. Accordingly, in many embodiments, the integrated circuit can have a small number of input signals compared to output signals with respect to the row driver and the opposite for the data line driver. In other embodiments, the control board and data board can be separate. As illustrated at FIG. 2, in some embodiments, row tape automated bond connector(s) 210 can be located at first image sensor sheet edge 206 and data tape automated bond connector(s) 211 can be located at second image sensor sheet edge 207.

Figure 3:
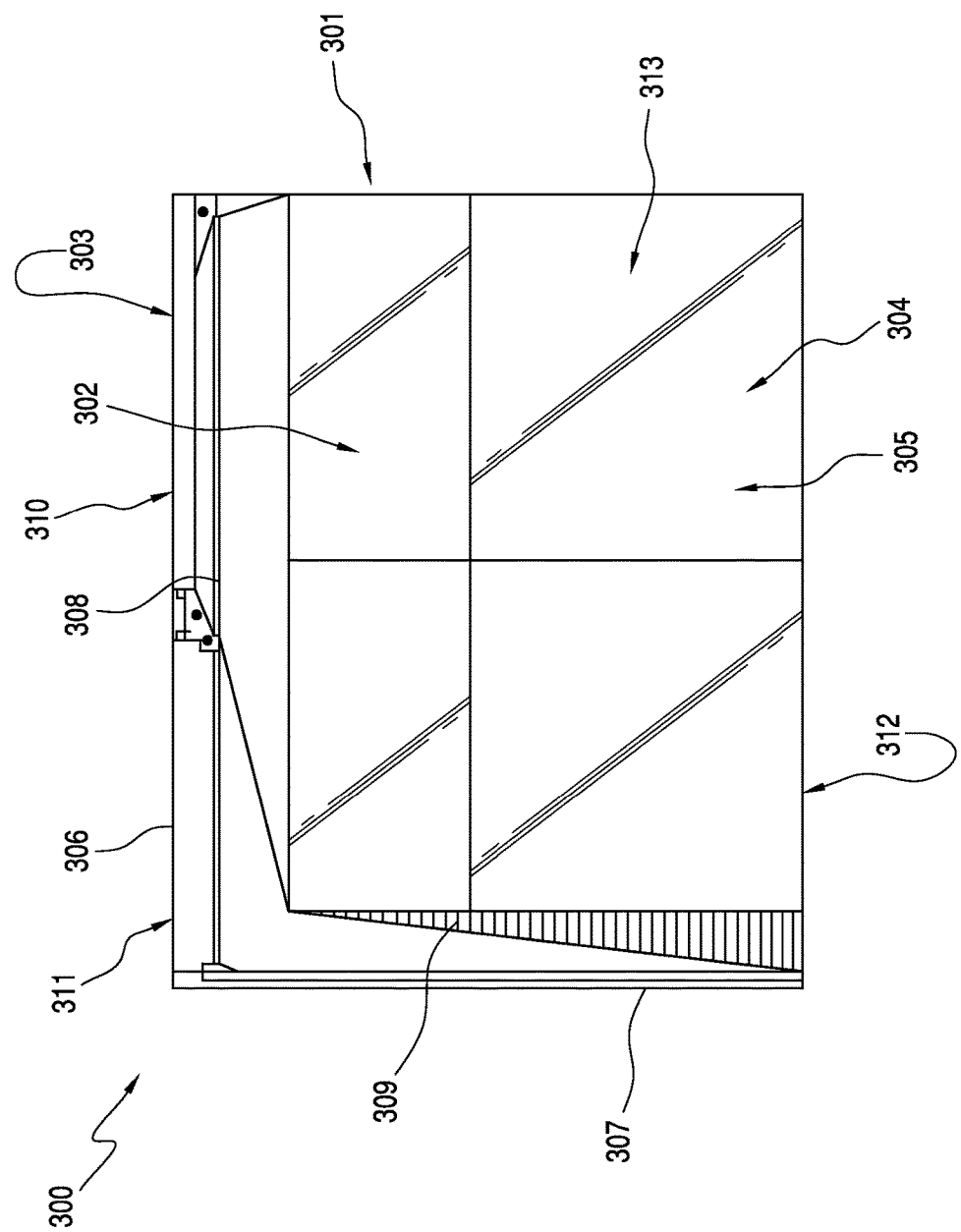
FIG. 3 illustrates another exemplary image sensor sheet, according to the embodiment of FIG. 1.

Meanwhile, FIG. 3 illustrates image sensor sheet 300, according to the embodiment of FIG. 1. Image sensor sheet 300 can be similar or identical to image sensor sheet 200 (FIG. 2). However, unlike image sensor sheet 200 (FIG. 2), for the embodiments of image sensor sheet 300, row tape automated bond connector(s) 310 and data tape automated bond connector(s) 311 can both be located at first image sensor sheet edge 306. The other elements in FIG. 3 correspond to similar elements in FIG. 2 that have reference numbers with the same last two digits.

Figure 4:
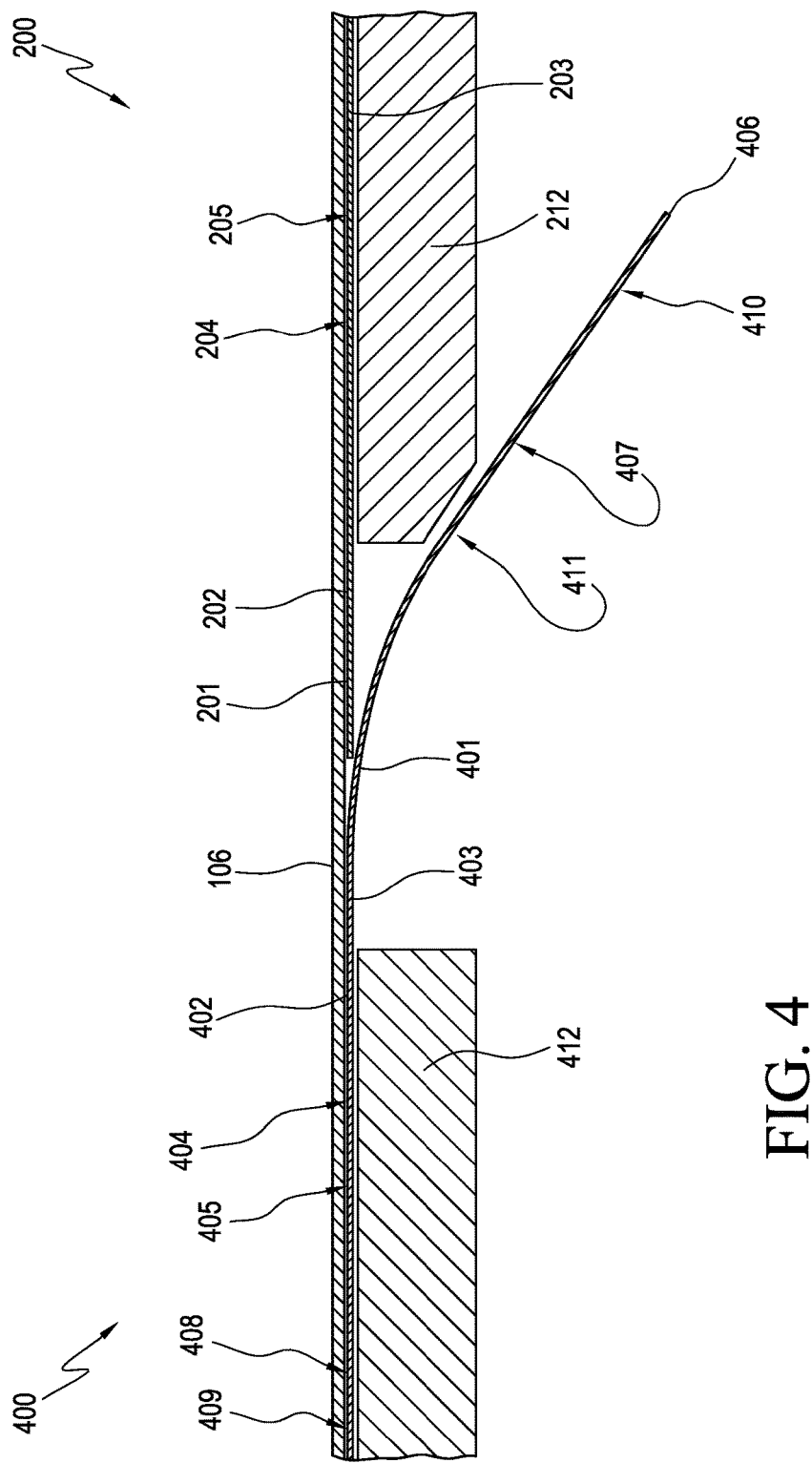
FIG. 4 illustrates a side view of the exemplary image sensor sheet of FIG. 2 with another exemplary sensor sheet, according to the embodiment of FIG. 1.

Turning ahead again in the drawings, FIG. 4 illustrates a side view of the exemplary image sensor sheet 200 with another exemplary image sensor sheet 400, according to the embodiment of FIG. 1. Image sensor sheet 400 can be similar or identical to image sensor sheet 200 (FIG. 2). Accordingly, elements of image sensor sheet 200 (FIG. 2) and image sensor sheet 400 that have reference numbers with the same last two digits can be similar or identical to each other. For example, image sensor sheet 400 can comprise flexible substrate layer 401, and flexible substrate layer 401 can comprise first flexible substrate side 402 and second flexible substrate side 403. Meanwhile, flexible substrate layer 401 can be similar or identical to flexible substrate layer 201 (FIG. 2), first flexible substrate side 402 can be similar or identical to first flexible substrate side 202 (FIG. 2), and second flexible substrate side 403 can be similar or identical to flexible substrate side 203 (FIG. 2).

Scintillator layer 106 (FIG. 1) can be located over image sensor array 101 (FIG. 1) such that scintillator layer 106 is flush with the active side of image sensor array 101 (FIG. 1). Accordingly, as shown at FIG. 4, scintillator layer 106 (FIG. 1) is located over and is flush with image sensor sheet 200 (FIG. 2) and image sensor sheet 400. Scintillator layer 106 (FIG. 1) can comprise any scintillator material configured to luminesce when exposed to electromagnetic radiation (e.g., ionizing radiation) that is also flexible so that it can flex along with image sensor array 101 (FIG. 1). For example, the scintillator material can comprise gadolinium oxide, polyethylene naphthalate (PEN), etc. In other examples, the scintillator material can comprise cesium iodide. In many embodiments, scintillator layer 106 can be configured to press multiple image sensor sheets 102 flat against one or more other image sensor sheets of multiple image sensor sheets 102, such as, for example, when one or more of the image sensor sheets of multiple image sensor sheets 102 overlap one or more other image sensor sheets of multiple image sensor sheets 102.

Further, flexible carrier layer 212 (FIG. 2) can be positioned sufficiently far apart from flexible carrier layer 412 to provide a groove into which flexible substrate layer 401 can recede when being partially overlapped by flexible substrate layer 201 (FIG. 2). As illustrated at FIG. 4, flexible substrate layer 201 (FIG. 2) and flexible substrate layer 401 remain approximately co-planar with each other even when flexible substrate layer 201 (FIG. 2) is partially overlapping flexible substrate layer 401. In some embodiments, as illustrated at FIG. 4, part of flexible carrier layer 212 (FIG. 2) can be removed to better facilitate the recession of flexible substrate layer 401 into the groove formed between flexible carrier layer 212 (FIG. 2) and flexible carrier layer 412.

Returning now to FIG. 2, row tape automated bond connector(s) 210 and/or data tape automated bond connector(s) 211 can be configured to stand off (e.g., project away) from image sensor sheet 200 and/or image sensor array 101 (FIG. 1), so that, for example, row tape automated bond connector(s) 210 and/or data tape automated bond connector(s) 211 do not press into flexible substrate 201 when set flush with scintillator layer 106 (FIG. 1). FIG. 4 illustrates row tape automated bond connector(s) 410 and/or data tape automated bond connector(s) 411 standing off from image sensor sheet 400 and/or image sensor array 101 (FIG. 1).

Meanwhile, returning to FIG. 1, in implementation, imaging system 100 can be positioned about the one or more objects to be imaged. For example, imaging system 100 can be bent to a desired curvature around the one or more objects. Then, electromagnetic radiation (e.g., ionizing radiation) can be emitted from an electromagnetic radiation source (e.g., an x-ray emitter) at the one or more objects and imaging system 100. Meanwhile, scintillator layer 106, which can be configured to luminesce in response to receiving electromagnetic radiation, can luminesce to provide photons to image sensor array 101, which can be detected by the multiple image sensors (e.g., multiple image sensors 204, multiple image sensors 304, multiple image sensors 404, etc.) of multiple image sensor sheets 102 in the form of imaging data about the object(s). The imaging data collected from multiple image sensor sheets 102 can then be electronically combined to form a composite digital image of the object(s) in a similar manner to that used in conventional systems for digital imaging. The composite digital image can be two or three dimensional, as desired, and can be displayed as a still frame or as video, as further desired. In effect, imaging system 100 can operate similarly to conventional systems for digital imaging but with numerous marked advantages over the same.

First, because imaging system 100 can be scaled to any desirable size simply by adding additional image sensor sheets of multiple image sensor sheets 102, there is no need to rapidly and/or mechanically reposition imaging system 100 about the object(s) being imaged. As indicated, imaging system 100 can simply be bent to cover the entire imaging area that would be imaged by repositioning a conventional system for digital imaging. As a result, imaging system 100 can provide imaging resolutions down to approximately 25 micrometers. Meanwhile, as indicated previously, imaging system 100 can be particularly well suited for tomography because it can be implemented to image the object(s) from effectively any angle that is desired. Further, because imaging system 100 can remain stationary for the entire imaging of the object(s), the imaging time can be substantially reduced because all the imaging can occur simultaneously. As a result, imaging with imaging system 100 can be faster and therefore, require less exposure to radiation than conventional systems for digital imaging. Further, because imaging system 100 can be scaled to any desirable size, imaging system 100 could even be wrapped around a portal for a cargo container or any other large object(s) that one desires to digitally image.

Meanwhile, as mentioned above, the relationship of multiple image sensors 102 to image sensor array 101 also provides numerous advantages to imaging system 100. For example, if an imaging array were simply enlarged in an attempt to provide the functionality of imaging system 100, the imaging readout speed would be reduced in proportion to the increased size of the imaging array. However, because each image sensor sheet of multiple image sensor sheets 102 operates independently and approximately simultaneously with each other, imaging readout speed can be left comparable with, if not improved, over conventional systems for digital imaging. Indeed, in many embodiments, imaging system 100 can provide imaging readout speeds at video frame rates (e.g., greater than or equal to approximately 30 frames per second). Furthermore, merely enlarging the imaging array would also proportionally increase electrically generated noise in the imaging array due to the increased length of the row and data lines. As mentioned previously, increased exposure to radiation could be needed to overcome the increased electrically generated noise in the imaging system. However, because each image sensor sheet of multiple image sensor sheets 102 can remain small in proportion to image sensor array 101 as a whole, electrically generated noise in the system can be minimized, and thereby, radiation exposure can be minimized as well. For example, where imaging system 100 comprises greater than or equal to approximately 2000 lines (e.g., multiple row lines 208 comprise greater than or equal to approximately 2000 row lines), imaging system 100 can comprise approximately 1500-2000 electrons of electrically generated noise per data line of multiple data lines 209.

Figure 5:
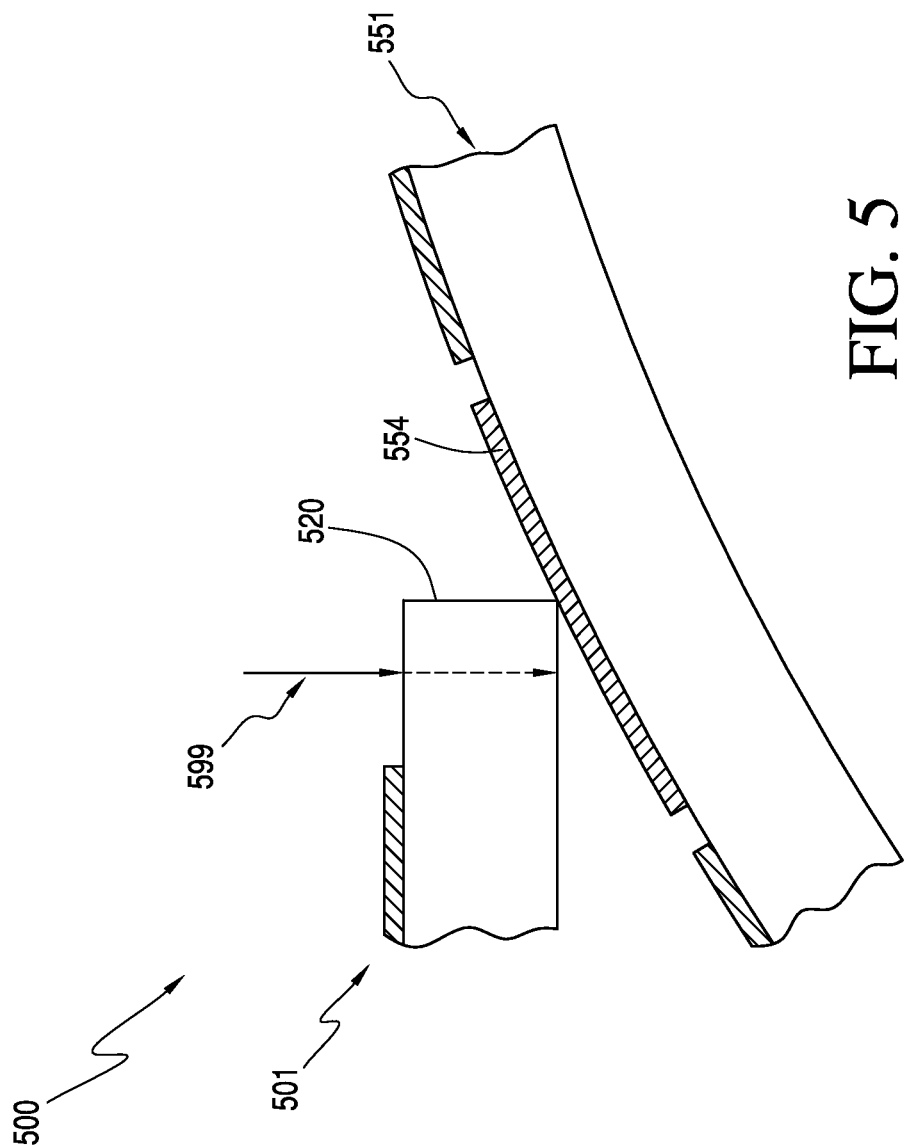
FIG. 5 illustrates a partial side view of an imaging system, according to an embodiment.

Further, as mentioned above, image sensor array 101 can also comprise an approximately constant and/or continuous pixel and/or dot pitch, even across the seams of image sensor array 101. The approximately constant and/or continuous pixel pitch can result, in part, because multiple image sensor sheets 102 can partially overlap each other while remaining approximately coplanar (e.g., prevent the formation of shadows and/or reducing any distances created between the multiple image sensors of multiple image sensor sheets 102) and/or, in part, because the flexible substrate layer (e.g., flexible substrate layer 201, flexible substrate layer 301, flexible substrate layer 401, etc.) of each image sensor sheet of multiple image sensor sheets 102 can be optically transparent so that photons emitted from scintillator layer 106 can pass through the flexible substrate of a first image sensor sheet (e.g., image sensor sheet 501 (FIG. 5)) of multiple image sensor sheets 102 that is partially overlapping a second image sensor sheet (e.g., image sensor sheet 551 (FIG. 5)), as illustrated at FIG. 5. Specifically, FIG. 5 illustrates a partial side view of imaging system 500, according to an embodiment. Imaging system 500 can be similar or identical to imaging system 100 (FIG. 1). Imaging system 500 comprises image sensor sheet 501 and image sensor sheet 551, which are shown where image sensor sheet 501 is overlapping image sensor sheet 551. Image sensor sheet 501 and image sensor sheet 551 can each be similar or identical to image sensor sheet 200 (FIG. 2), image sensor sheet 300 (FIG. 3), and/or image sensor sheet 400 (FIG. 4). As further illustrated at FIG. 5, photons 599 are able to pass through image sensor sheet 501 to reach image sensor 554 of image sensor sheet 551 such that the overlap does not create gaps in the x-ray images provided by imaging system 500. Image sensor 554 can be similar or identical to any one of multiple image sensors 204 (FIG. 2). FIG. 5 further illustrates cut 520 of image sensor sheets 501.

Returning once again to FIG. 1, the minimal thickness and/or the effective transparency of multiple image sensor sheets 102 also provides for relative ease of manufacturing imaging system 100 over conventional systems for digital imaging. For example, cutting each image sensor sheet of multiple image sensor sheets 102 can require lower degrees of precision than would be necessary when cutting device layers for the conventional systems because multiple image sensor sheets 102 can partially overlap each other. Further, to the same end, aligning each image sensor sheet of multiple image sensor sheets 102 can also require less precision because of overlapping image sensors located over flexible substrate layer 201 of multiple imaging sensor sheets 102. Further still, manufacturing yields of imaging system 100 can also be improved over conventional systems for digital imaging as a result of the smaller individual sizes of multiple image sensor sheets 102. Not to mention, if one image sensor sheet of multiple image sensor sheets 102 stops working properly, the image sensor sheet can be individually replaced instead of having to replace all of image sensor array 101. Accordingly, these improved manufacturing yields can at least offset additional costs of supplying application-specific integrated circuits and tape automated bonding of the row and data lines of multiple image sensor sheets 102.

Imaging system 100 and/or image sensor array 101 can also be implemented for applications other than and/or in addition to digital imaging. For example, where scintillator layer 106 is omitted, image sensor array 101 and/or multiple image sensors 204 (FIG. 2) can be configured to provide other types of image sensing. In some embodiments, image sensor array 101 can be configured to detect the approximate location of a laser beam emitted at image sensor array 101. In specific examples, one or more of image sensor array 101 can be arranged on an exterior of an object (e.g., a vehicle) in order to detect the approximate location of a laser beam emitted at the object.

Figure 6:
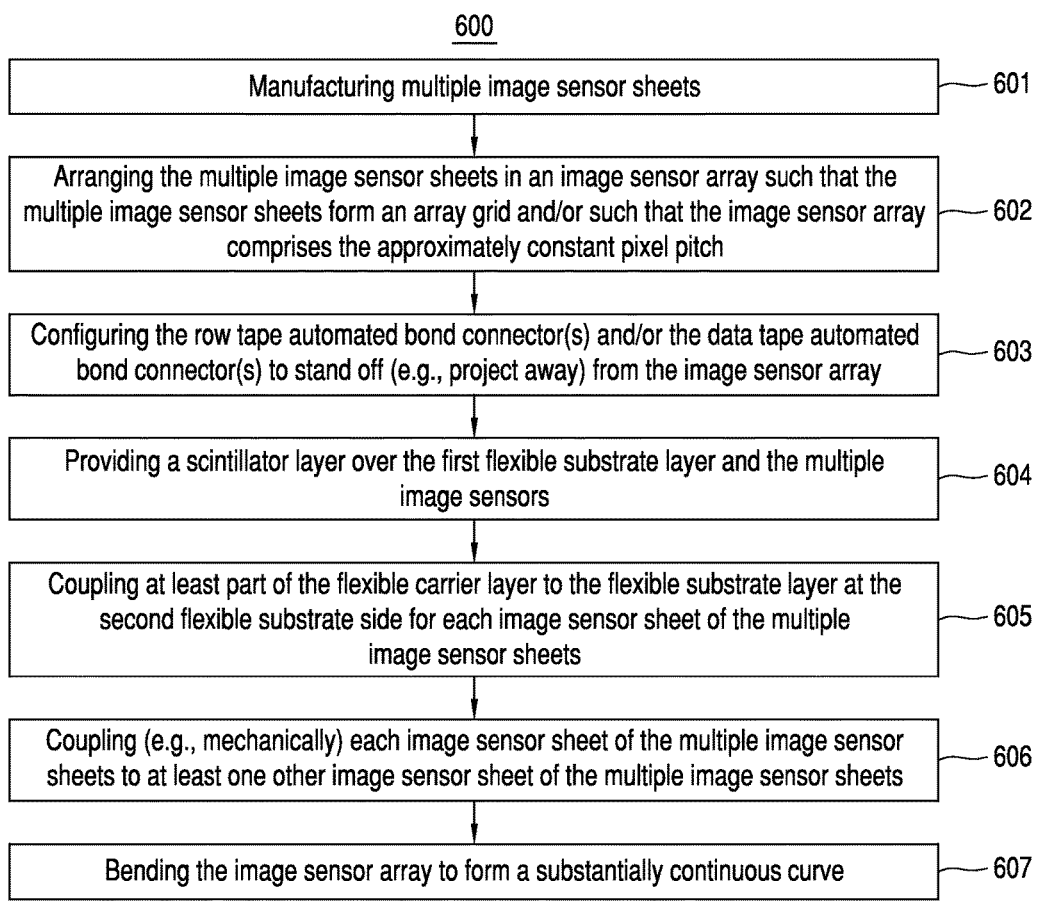
FIG. 6 illustrates a flow chart for an embodiment of a method of manufacturing an imaging system.

Turning ahead now in the drawings, FIG. 6 illustrates a flow chart for an embodiment of method 600 of manufacturing an imaging system. Method 600 is merely exemplary and is not limited to the embodiments presented herein. Method 600 can be employed in many different embodiments or examples not specifically depicted or described herein. In some embodiments, the activities, the procedures, and/or the processes of method 600 can be performed in the order presented. In other embodiments, the activities, the procedures, and/or the processes of method 600 can be performed in any other suitable order. In still other embodiments, one or more of the activities, the procedures, and/or the processes in method 600 can be combined or skipped. The imaging system can be similar or identical to imaging system 100 (FIG. 1) and/or imaging system 500 (FIG. 5).

Figure 7:
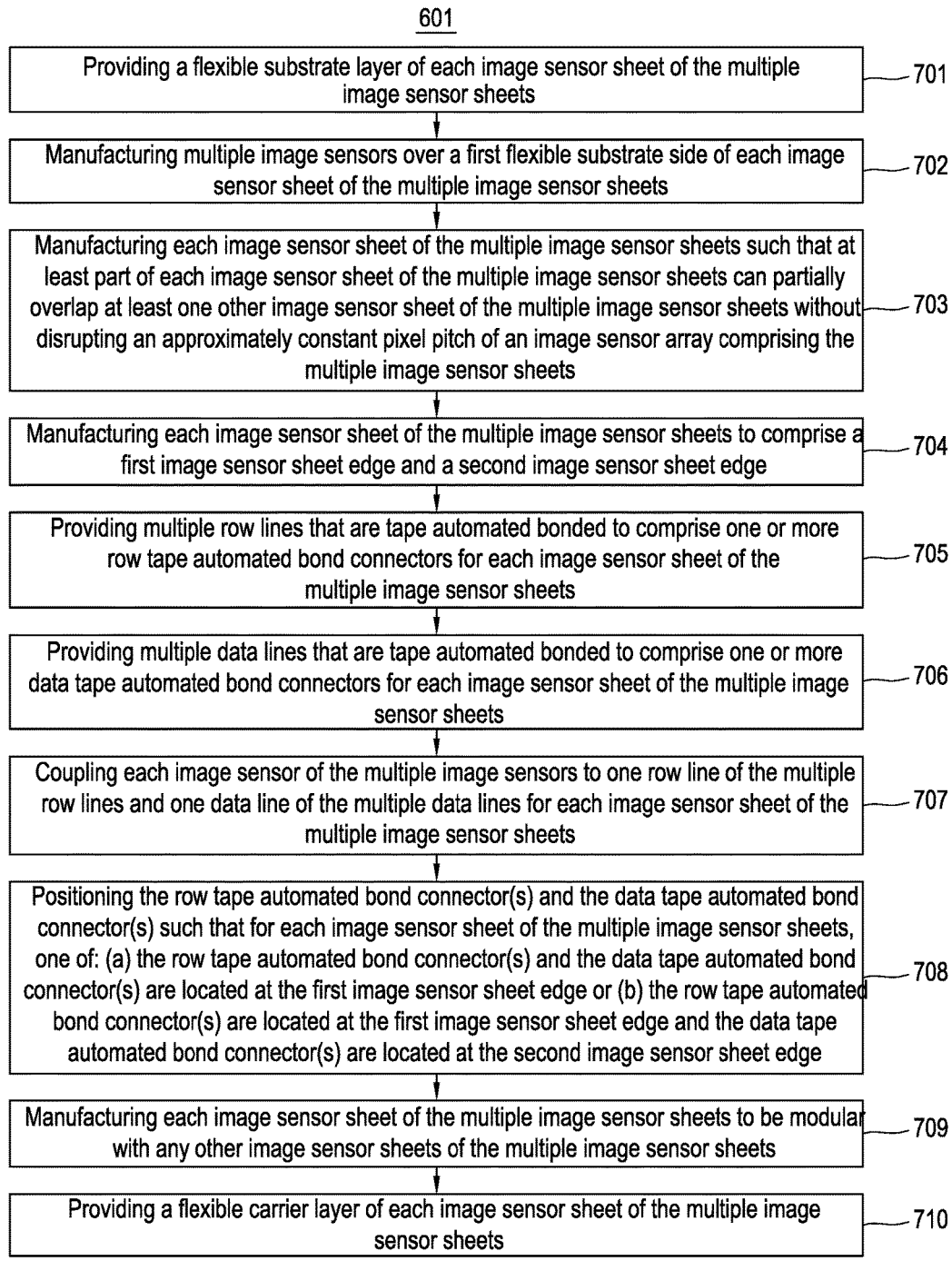
FIG. 7 illustrates an exemplary activity of manufacturing multiple image sensor sheets, according to the embodiment of FIG. 6.

Method 600 can comprise activity 601 of manufacturing multiple image sensor sheets. The multiple image sensor sheets can be similar or identical to multiple image sensor sheets 102 (FIG. 1). FIG. 7 illustrates an exemplary activity 601.

Referring to FIG. 7, activity 601 can comprise activity 701 of providing a flexible substrate layer of each image sensor sheet of the multiple image sensor sheets. The flexible substrate layer can be similar or identical to flexible substrate layer 201 (FIG. 2), flexible substrate layer 301 (FIG. 3), and/or flexible substrate layer 401 (FIG. 4).

Further, activity 601 can comprise activity 702 of manufacturing multiple image sensors over a first flexible substrate side of each image sensor sheet of the multiple image sensor sheets 102. The multiple image sensors can be similar or identical to multiple image sensors 204 (FIG. 2), multiple image sensors 304 (FIG. 3), and/or multiple image sensors 404 (FIG. 4).

Activity 601 can comprise activity 703 of manufacturing each image sensor sheet of multiple image sensor sheets 102 such that at least part of each image sensor sheet of multiple image sensor sheets 102 can partially overlap at least one other image sensor sheet of multiple image sensor sheets 102 without disrupting an approximately constant pixel pitch of image sensor array 101 comprising multiple image sensor sheets 102. The image sensor array can be similar or identical to image sensory array 101 (FIG. 1).

Activity 601 can comprise activity 704 of manufacturing each image sensor sheet of multiple image sensor sheets 102 to comprise a first image sensor sheet edge and a second image sensor sheet edge. The first image sensor sheet edge can be similar or identical to first image sensor sheet edge 206 (FIG. 2), first image sensor sheet edge 306 (FIG. 3), and/or first image sensor sheet edge 406 (FIG. 4). Further, the second image sensor sheet edge can be similar or identical to second image sensor sheet edge 207 (FIG. 2), second image sensor sheet edge 307 (FIG. 3), and/or second image sensor sheet edge 407 (FIG. 4).

Activity 601 can comprise activity 705 of providing multiple row lines that are tape automated bonded to comprise one or more row tape automated bond connectors for each image sensor sheet of the multiple image sensor sheets. The multiple row lines can be similar or identical to multiple row lines 208 (FIG. 2), multiple row lines 308 (FIG. 3), and/or multiple row lines 408 (FIG. 4). Further, the row tape automated bond connector(s) can be similar or identical to row tape automated bond connector(s) 210 (FIG. 2), row tape automated bond connector(s) 310 (FIG. 3), and/or row tape automated bond connector(s) 410 (FIG. 4).

Activity 601 can comprise activity 706 of providing multiple data lines that are tape automated bonded to comprise one or more data tape automated bond connector(s) for each image sensor sheet of the multiple image sensor sheets. The multiple data lines can be similar or identical to multiple data lines 209 (FIG. 2), multiple data lines 309 (FIG. 3), and/or multiple data lines 409 (FIG. 4). Further, the data tape automated bond connector can be similar or identical to data tape automated bond connector(s) 211 (FIG. 2), data tape automated bond connector(s) 311 (FIG. 3), and/or data tape automated bond connector(s) 411 (FIG. 4).

Activity 601 can comprise activity 707 of coupling each image sensor of the multiple image sensors to one row line of the multiple row lines and one data line of the multiple data lines for each image sensor sheet of multiple image sensor sheets 102. For example, activity 707 can comprise coupling a flat panel image detector of each image sensor of the multiple image sensors to one row line of the multiple row lines and one data line of the multiple data lines for each image sensor sheet of multiple image sensor sheets 102. Each of the flat panel image detectors can be similar or identical to any one of the flat panel image detectors of multiple flat panel image detectors 205 (FIG. 2), multiple flat panel image detectors 305 (FIG. 3), and/or multiple flat panel image detectors 405 (FIG. 4).

Activity 601 can comprise activity 708 of positioning the row tape automated bond connector(s) and the data tape automated bond connector(s) such that for each image sensor sheet of multiple image sensor sheets 102, one of: (a) the row tape automated bond connector(s) and the data tape automated bond connector(s) are located at the first image sensor sheet edge or (b) the row tape automated bond connector(s) are located at the first image sensor sheet edge and the data tape automated bond connector(s) are located at the second image sensor sheet edge.

Activity 601 can comprise activity 709 of manufacturing each image sensor sheet of multiple image sensor sheets 102 to be modular with any other image sensor sheets of multiple image sensor sheets 102. In some embodiments, one or more of activities 702 through 709 can occur simultaneously.

Activity 601 can comprise activity 710 of providing a flexible carrier layer of each image sensor sheet of multiple image sensor sheets 102. The flexible carrier layer can be similar or identical to flexible carrier layer 212 (FIG. 2), flexible carrier layer 312 (FIG. 3), and/or flexible carrier layer 412 (FIG. 4). In some embodiments, activity 710 can be omitted. In further embodiments, one or more of activities 702 through 709 can be omitted, such as, for example, where the flexible substrate layer are provided as pre-manufactured according to one or more of activities 702 through 709.

Referring now back to FIG. 6, method 600 can comprise activity 602 of arranging the multiple image sensor sheets in an image sensor array such that the multiple image sensor sheets form an array grid and/or such that the image sensor array comprises the approximately constant pixel pitch. The array grid can be similar or identical to array grid 103 (FIG. 1). In some embodiments, activity 602 can comprise arranging the multiple image sensor sheets in the image sensor array such that the array grid comprises an array grid sheet length and an array grid sheet width and such that at least one of the array grid sheet length or the array grid sheet width comprises at least three image sensor sheets. The array grid sheet length can be similar or identical to array grid sheet length 104 (FIG. 1), and the array grid sheet width can be similar or identical to array grid sheet width 105 (FIG. 1).

Method 600 can comprise activity 603 of configuring the row tape automated bond connector(s) and/or the data tape automated bond connector(s) to stand off (e.g., project away) from the image sensor array.

Method 600 can comprise activity 604 of providing a scintillator layer over the first flexible substrate layer and the multiple image sensors. The scintillator layer can be similar or identical to scintillator layer 106 (FIG. 1).

Method 600 can comprise activity 605 of coupling at least part of the flexible carrier layer to the flexible substrate layer at the second flexible substrate side for each image sensor sheet of the multiple image sensor sheets. In some embodiments, activity 605 can be omitted, such as, for example, where activity 710 is omitted, and vice versa.

Method 600 can comprise activity 606 of coupling (e.g., mechanically) each image sensor sheet of the multiple image sensor sheets to at least one other image sensor sheet of the multiple image sensor sheets, such as, for example, with an optically transparent tape and/or adhesive, as described above with respect to imaging system 100 (FIG. 1). In some embodiments, activity 606 can be omitted.

Method 600 can comprise activity 607 of bending the image sensor array to form a substantially continuous curve. In some embodiments, activity 607 can be omitted.

Figure 8:
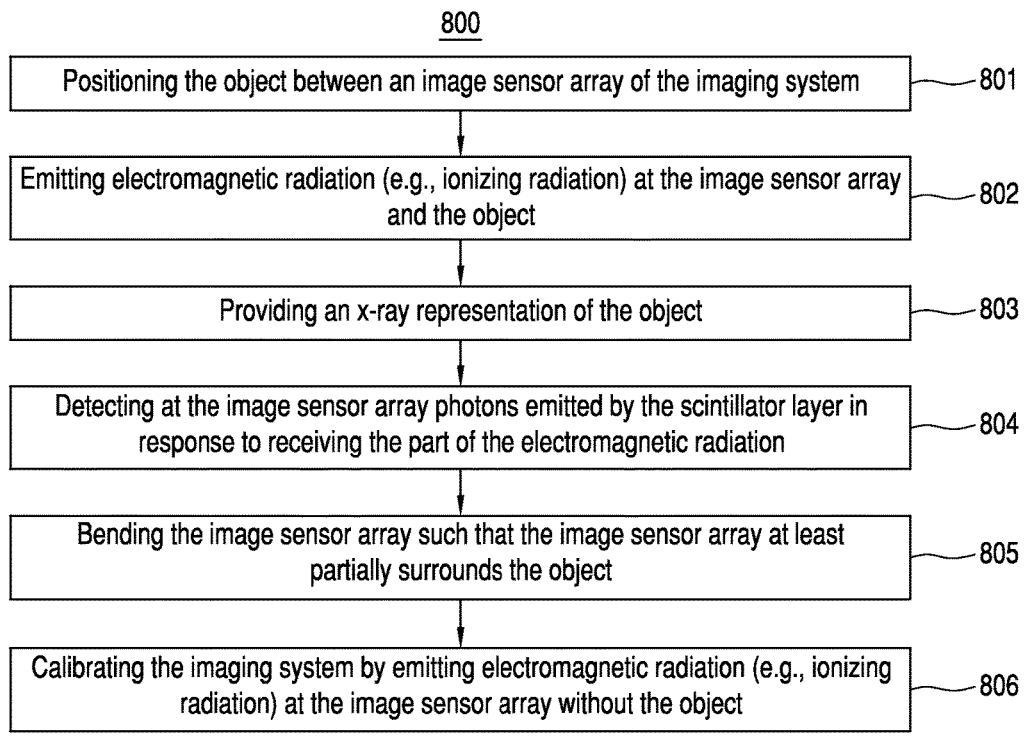
FIG. 8 illustrates a flow chart for an embodiment of a method of imaging an object with an imaging system.

FIG. 8 illustrates a flow chart for an embodiment of method 800 of imaging an object with an imaging system. Method 800 is merely exemplary and is not limited to the embodiments presented herein. Method 800 can be employed in many different embodiments or examples not specifically depicted or described herein. In some embodiments, the activities, the procedures, and/or the processes of method 800 can be performed in the order presented. In other embodiments, the activities, the procedures, and/or the processes of method 800 can be performed in any other suitable order. In still other embodiments, one or more of the activities, the procedures, and/or the processes in method 800 can be combined or skipped. In many embodiments, the imaging system can be similar or identical to imaging system 100 (FIG. 1) and/or imaging system 500 (FIG. 5). Meanwhile, the object can be similar or identical to one of the object(s) described above with respect to imaging system 100 (FIG. 1).

Method 800 can comprise activity 801 of positioning the object between an image sensor array of the imaging system and an emitter of electromagnetic radiation. The image sensor array can be similar or identical to image sensor array 101 (FIG. 1).

Method 800 can comprise activity 802 of emitting electromagnetic radiation (e.g., ionizing radiation) from the emitter of the electromagnetic radiation at the image sensor array and the object. In some embodiments, activity 802 can comprise receiving part of the electromagnetic radiation at a scintillator layer positioned between the image sensor array and the object. The scintillator layer can be similar or identical to scintillator layer 106 (FIG. 1).

Figure 9:
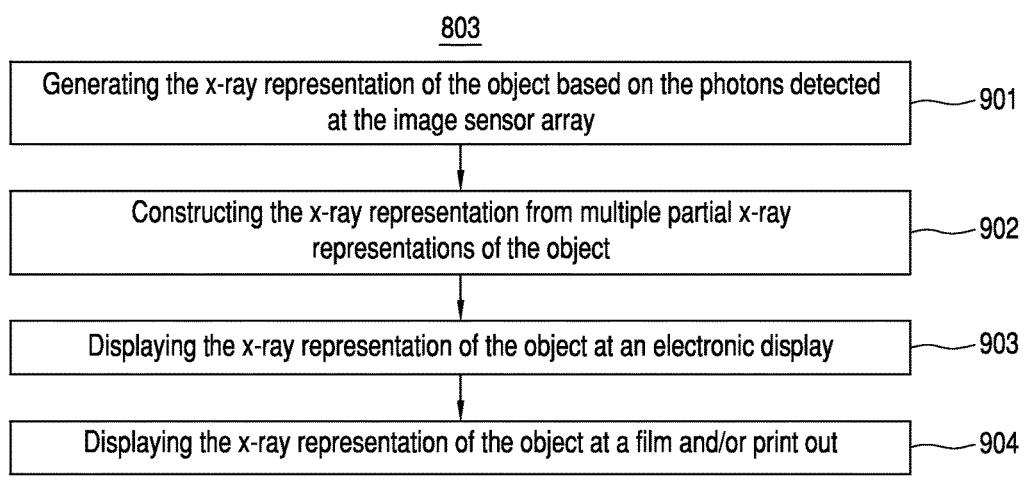
FIG. 9 illustrates an exemplary activity of providing an x-ray representation of the object, according to the embodiment of FIG. 8.

Method 800 can comprise activity 803 of providing an x-ray representation of the object. FIG. 9 illustrates an exemplary activity 803.

Referring to FIG. 9, activity 803 can comprise activity 901 of generating the x-ray representation of the object based on the photons detected at the image sensor array.

Activity 803 can comprise activity 902 of constructing the x-ray representation from multiple partial x-ray representations of the object. In many embodiments, each of the multiple partial x-ray representations can be generated based on the photons detected at different ones of at least two of image sensor sheets of multiple image sensor sheets of the image sensor array. The multiple image sensor sheets can be similar or identical to multiple image sensor sheets 102 (FIG. 1). In some embodiments, activity 902 can be performed as part of activity 901.

Activity 803 can comprise activity 903 of displaying the x-ray representation of the object at an electronic display. The electronic display can comprise any suitable electronic display (e.g., a flat panel electronic display, a cathode ray tube electronic display, etc.).

Activity 803 can comprise activity 904 of displaying the x-ray representation of the object at a film and/or print out. In some embodiments, activity 904 can be omitted. In other embodiments, activity 903 can be omitted.

Returning now to FIG. 8, method 800 can comprise activity 804 of detecting at the image sensor array photons emitted by the scintillator layer in response to receiving the part of the electromagnetic radiation.

In some embodiments, method 800 can comprise activity 805 of bending the image sensor array such that the image sensor array at least partially surrounds the object. In some embodiments, activity 805 can be performed prior to one or more of activities 801 through 804.

In some embodiments, method 800 can comprise activity 806 of calibrating the imaging system by emitting electromagnetic radiation (e.g., ionizing radiation) from the emitter of the electromagnetic radiation at the image sensor array without the object. In some embodiments, activity 806 can be performed prior to one or more of activities 801 through 805. In the same or different embodiments, activity 803 can be performed after one or more of activities 804 through 806.

Figure 10:
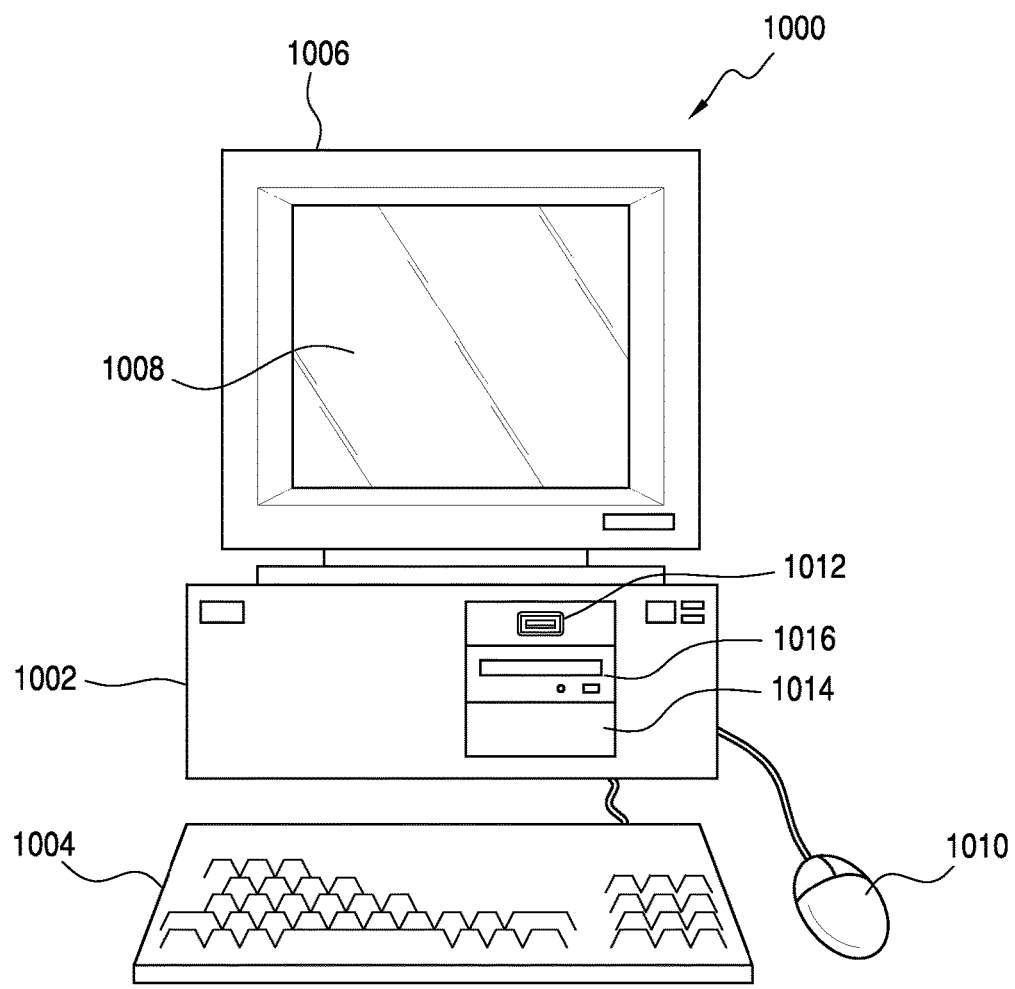
FIG. 10 illustrates a computer system that is suitable for implementing part of the functionality of the imaging systems of FIGS. 1 and 5.
Figure 11:
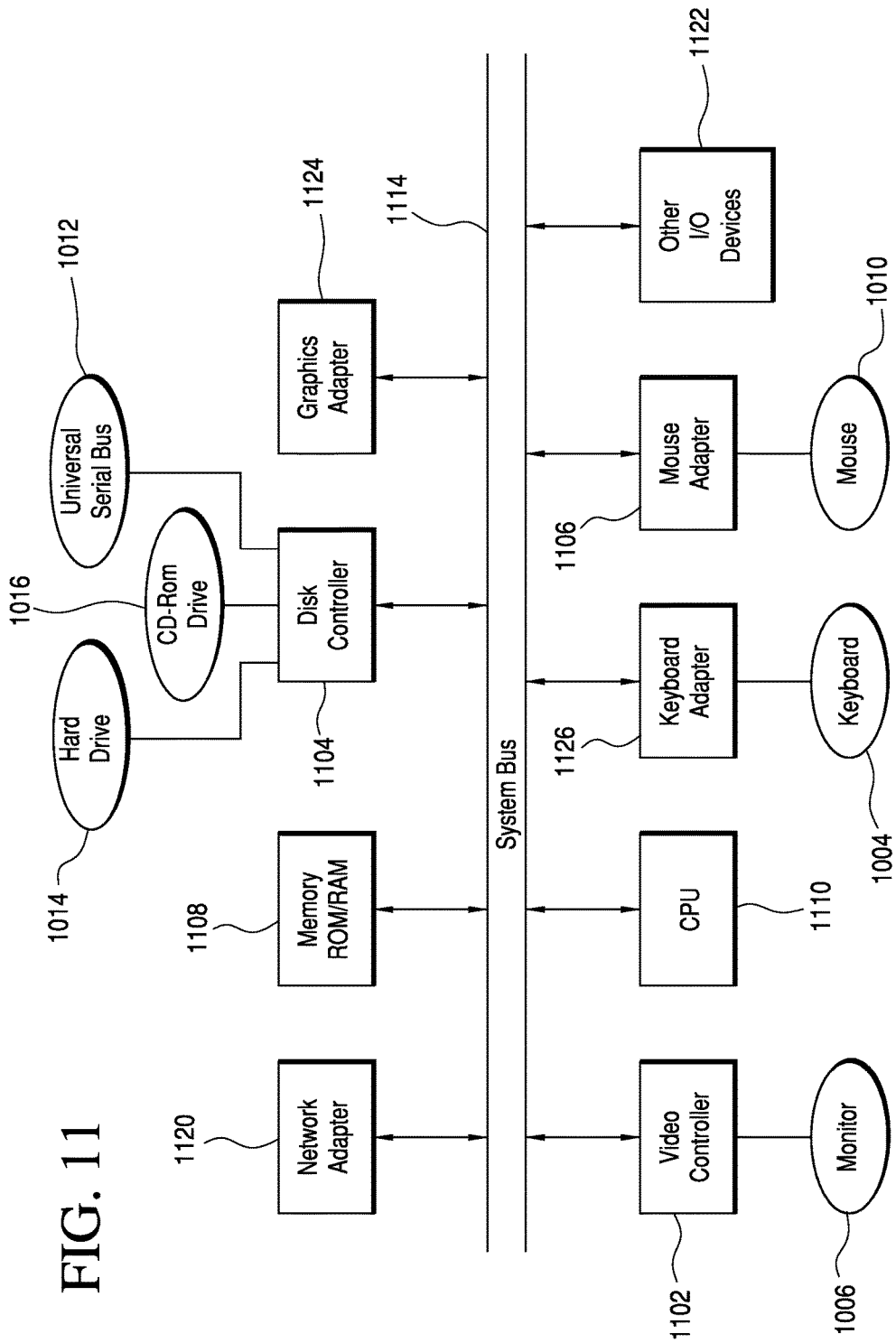
FIG. 11 illustrates a representative block diagram of an example of the elements included in the circuit boards inside chassis of the computer system of FIG. 10.

Turning ahead in the drawing, FIG. 10 illustrates an exemplary embodiment of computer system 1000, all of which or a portion of which can be suitable for implementing part of the functionality of imaging system 100 (FIG. 1) and/or imaging system 500 (FIG. 5) as well as methods 600 (FIG. 6) and 800 (FIG. 8) and/or any of the various procedures, processes, and/or activities of methods 600 (FIG. 6) and 800 (FIG. 8). Computer system 1000 includes chassis 1002 containing one or more circuit boards (not shown), Universal Serial Bus (USB) 1012, Compact Disc Read-Only Memory (CD-ROM) and/or Digital Video Disc (DVD) drive 1016, and hard drive 1014. A representative block diagram of the elements included on the circuit boards inside chassis 1002 is shown in FIG. 10. Central processing unit (CPU) 1110 in FIG. 11 is coupled to system bus 1114 in FIG. 11. In various embodiments, the architecture of CPU 1110 can be compliant with any of a variety of commercially distributed architecture families.

System bus 1114 also is coupled to memory 1108, where memory 1108 includes both read only memory (ROM) and random access memory (RAM). Non-volatile portions of memory 1108 or the ROM can be encoded with a boot code sequence suitable for restoring computer system 1000 (FIG. 10) to a functional state after a system reset. In addition, memory 1108 can include microcode such as a Basic Input-Output System (BIOS). In some examples, the one or more storage modules of the various embodiments disclosed herein can include memory 1108, USB 1012 (FIGS. 10-11), hard drive 1014 (FIGS. 10-11), and/or CD-ROM or DVD drive 1016 (FIGS. 10-11). In the same or different examples, the one or more storage modules of the various embodiments disclosed herein can comprise an operating system, which can be a software program that manages the hardware and software resources of a computer and/or a computer network. The operating system can perform basic tasks such as, for example, controlling and allocating memory, prioritizing the processing of instructions, controlling input and output devices, facilitating networking, and managing files. Examples of common operating systems can include Microsoft® Windows, Mac® operating system (OS), UNIX® OS, and Linux® OS.

As used herein, "processor" and/or "processing module" means any type of computational circuit, such as but not limited to a microprocessor, a microcontroller, a controller, a complex instruction set computing (CISC) microprocessor, a reduced instruction set computing (RISC) microprocessor, a very long instruction word (VLIW) microprocessor, a graphics processor, a digital signal processor, or any other type of processor or processing circuit capable of performing the desired functions.

In the depicted embodiment of FIG. 11, various I/O devices such as disk controller 1104, graphics adapter 1124, video controller 1102, keyboard adapter 1126, mouse adapter 1106, network adapter 1120, and other I/O devices 1122 can be coupled to system bus 1114. Keyboard adapter 1126 and mouse adapter 1106 are coupled to keyboard 1004 (FIGS. 10-11) and mouse 1010 (FIGS. 10-11), respectively, of computer system 1000 (FIG. 10). While graphics adapter 1124 and video controller 1102 are indicated as distinct units in FIG. 11, video controller 1102 can be integrated into graphics adapter 1124, or vice versa in other embodiments. Video controller 1102 is suitable for refreshing monitor 1006 (FIGS. 10-11) to display images on a screen 1008 (FIG. 10) of computer system 1000 (FIG. 10). Disk controller 1104 can control hard drive 1014 (FIGS. 10-11), USB 1012 (FIGS. 10-11), and CD-ROM drive 1016 (FIGS. 10-11). In other embodiments, distinct units can be used to control each of these devices separately.

In some embodiments, network adapter 1120 can be part of a WNIC (wireless network interface controller) card (not shown) plugged or coupled to an expansion port (not shown) in computer system 1000. In other embodiments, the WNIC card can be a wireless network card built into computer system 1000. A wireless network adapter can be built into computer system 1000 by having wireless Ethernet capabilities integrated into the motherboard chipset (not shown), or implemented via a dedicated wireless Ethernet chip (not shown), connected through the PCI (peripheral component interconnector) or a PCI express bus. In other embodiments, network adapter 1120 can be a wired network adapter.

Although many other components of computer system 1000 (FIG. 10) are not shown, such components and their interconnection are well known to those of ordinary skill in the art. Accordingly, further details concerning the construction and composition of computer system 1000 and the circuit boards inside chassis 1002 (FIG. 10) are not discussed herein.

When computer system 1000 in FIG. 10 is running, program instructions stored on a USB-equipped electronic device connected to USB 1012, on a CD-ROM or DVD in CD-ROM and/or DVD drive 1016, on hard drive 1014, or in memory 1108 (FIG. 11) are executed by CPU 1110 (FIG. 11). A portion of the program instructions, stored on these devices, can be suitable for carrying out at least part of imaging system 100 (FIG. 1), imaging system 500 (FIG. 5), method 600 (FIG. 6) and/or method 800 (FIG. 8).

In some embodiments, a frame grabber board can be coupled to system bus 1114, so that, for example, computer system 1000 comprises the frame grabber board. Multiple data lines 209 (FIG. 2), multiple data lines 309 (FIG. 3), and/or multiple data lines 409 (FIG. 4) for one or more image sensor sheets of multiple image sensor sheets 102 (FIG. 1) can be coupled to the frame grabber board. Computer system 1000 can receive image data provided from multiple data lines 209 (FIG. 2), multiple data lines 309

(FIG. 3), and/or multiple data lines 409 (FIG. 4) and manipulate the image data, such as, for example, removing bad image data provided by malfunctioning data lines, improving contrast, removing electronically generated noise, electronically combining image data from multiple image sensor sheets 102 (FIG. 1) to form a composite digital image. Where computer system 1000 is operating with multiple other computer systems, as described below, the frame grabber boards of each computer system can be networked together to operate cooperatively.

Although computer system 1000 is illustrated as a desktop computer in FIG. 10, there can be examples where computer system 1000 may take a different form factor (e.g., a mobile electronic device, a laptop computer) while still having functional elements similar to those described for computer system 1000. In some embodiments, computer system 1000 may comprise a single computer, a single server, or a cluster or collection of computers or servers, or a cloud of computers or servers. Typically, a cluster or collection of servers can be used when the demand on computer system 1000 exceeds the reasonable capability of a single server or computer.

Although the invention has been described with reference to specific embodiments, it will be understood by those skilled in the art that various changes may be made without departing from the spirit or scope of the invention. Accordingly, the disclosure of embodiments of the invention is intended to be illustrative of the scope of the invention and is not intended to be limiting. It is intended that the scope of the invention shall be limited only to the extent required by the appended claims. For example, to one of ordinary skill in the art, it will be readily apparent that activities 601 through 607 of FIG. 6, activities 701 through 710 of FIG. 7, activities 801 through 806 of FIG. 8, and/or activities 901 through 904 of FIG. 9 may be comprised of many different activities and may be performed by many different modules, and in many different orders, and that any element of FIGS. 1-12 may be modified, and that the foregoing discussion of certain of these embodiments does not necessarily represent a complete description of all possible embodiments.

All elements claimed in any particular claim are essential to the embodiment claimed in that particular claim. Consequently, replacement of one or more claimed elements constitutes reconstruction and not repair. Additionally, benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims, unless such benefits, advantages, solutions, or elements are stated in such claim.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

What is claimed is:

1. An imaging system comprising:
an image sensor array comprising multiple image sensor sheets configured in an array grid;
wherein:
each image sensor sheet of the multiple image sensor sheets comprises a flexible substrate layer;
the flexible substrate layer comprises a first flexible substrate side and a second flexible substrate side opposite the first flexible substrate side;
each image sensor sheet of the multiple image sensor sheets comprises multiple image sensors over the first flexible substrate side, the multiple image sensors comprising multiple flat panel image detectors configured in a sheet grid;
the image sensor array comprises an approximately constant pixel pitch; and
at least part of at least one image sensor sheet of the multiple image sensor sheets overlaps at least part of at least one other image sensor sheet of the multiple image sensor sheets without disrupting the approximately constant pixel pitch of the image sensor array.

2. The imaging system of claim 1, wherein:
the array grid comprises an array grid sheet length and an array grid sheet width; and
at least one of the array grid sheet length or the array grid sheet width comprises at least three image sensor sheets.

3. The imaging system of claim 1, wherein:
each image sensor sheet of the multiple image sensor sheets comprises a first image sensor sheet edge, a second image sensor sheet edge, multiple row lines, and multiple data lines;
each image sensor of the multiple image sensors is coupled to one row line of the multiple row lines and one data line of the multiple data lines;
the multiple row lines are tape automated bonded at one or more row tape automated bond connectors, and the multiple data lines are tape automated bonded at one or more data tape automated bond connectors; and
one of: (a) the one or more row tape automated bond connectors and the one or more data tape automated bond connectors are located at the first image sensor sheet edge or (b) the one or more row tape automated bond connectors are located at the first image sensor sheet edge, and the one or more data tape automated bond connectors are located at the second image sensor sheet edge.

4. The imaging system of claim 3, wherein:
the one or more row tape automated bond connectors and the one or more data tape automated bond connectors are configured to stand off from the image sensor array.

5. The imaging system of claim 1, further comprising:
a scintillator layer over the first flexible substrate layer and the multiple image sensors.

6. The imaging system of claim 1, wherein:
each image sensor sheet of the multiple image sensor sheets comprises a flexible carrier layer; and
at least part of the flexible carrier layer is coupled to the flexible substrate layer at the second flexible substrate side.

7. The imaging system of claim 1, wherein:
each image sensor sheet of the multiple image sensor sheets is coupled to one or more other image sensor sheets of the multiple image sensor sheets.

8. The imaging system of claim 1, wherein at least one of:
the image sensor array is configured to form a substantially continuous curve; or
each image sensor sheet of the multiple image sensor sheets is modular with any other image sensor sheets of the multiple image sensor sheets.

9. The imaging system of claim 1, wherein at least one of:
the flexible substrate layer comprises polyethylene naphthalate or polyethylene terephthalate; or
the flexible substrate layer is optically transparent.

10. A method of manufacturing an imaging system, the method comprising:
manufacturing multiple image sensor sheets; and
arranging the multiple image sensor sheets in an image sensor array such that the multiple image sensor sheets form an array grid and such that the image sensor array comprises an approximately constant pixel pitch;
wherein:
manufacturing the multiple image sensor sheets comprises:
providing a flexible substrate layer of each image sensor sheet of the multiple image sensor sheets, the flexible substrate layer comprising a first flexible substrate side and a second flexible substrate side opposite the first flexible substrate side; and
manufacturing multiple image sensors over the first flexible substrate side of each image sensor sheet of the multiple image sensor sheets, the multiple image sensors comprising multiple flat panel image detectors configured in a sheet grid; and
for each image sensor sheet of the multiple image sensor sheets:
manufacturing each image sensor sheet to comprise a first image sensor sheet edge and a second image sensor sheet edge;
providing multiple row lines that are tape automated bonded to comprise one or more row tape automated bond connectors;
providing multiple data lines that are tape automated bonded to comprise one or more data tape automated bond connectors;
coupling each image sensor of the multiple image sensors to one row line of the multiple row lines and one data line of the multiple data lines; and
positioning the one or more row tape automated bond connectors and the one or more data tape automated bond connectors such that one of: (a) the one or more row tape automated bond connectors and the one or more data tape automated bond connectors are located at the first image sensor sheet edge or (b) the one or more row tape automated bond connectors are located at the first image sensor sheet edge, and the one or more data tape automated bond connectors are located at the second image sensor sheet edge.

11. The method of claim 10, wherein at least one of:
arranging the multiple image sensor sheets in the image sensor array such that the multiple image sensor sheets form the array grid comprises arranging the multiple image sensor sheets such that at least part of at least one image sensor sheet of the multiple image sensor sheets overlaps at least part of at least one other image sensor sheet of the multiple image sensor sheets without disrupting the approximately constant pixel pitch of the image sensor array; or
arranging the multiple image sensor sheets in the image sensor array such that the multiple image sensor sheets form the array grid comprises arranging the multiple image sensor sheets in the image sensor array such that the array grid comprises an array grid sheet length and an array grid sheet width and such that at least one of the array grid sheet length or the array grid sheet width comprises at least three image sensor sheets.

12. The method of claim 10, wherein at least one of:
the method further comprises providing a scintillator layer over the flexible substrate layer and the multiple image sensors;
manufacturing the multiple image sensor sheets comprises providing a flexible carrier layer of each image sensor sheet of the multiple image sensor sheets, and the method further comprises coupling at least part of the flexible carrier layer to the flexible substrate layer at the second flexible substrate side for each image sensor sheet of the multiple image sensor sheets; or
the method further comprises coupling each image sensor sheet of the multiple image sensor sheets to at least one other image sensor sheet of the multiple image sensor sheets.

13. The method of claim 10, wherein at least one of:
the method comprises bending the image sensor array to form at least one substantially continuous curve;
manufacturing the multiple image sensor sheets comprises manufacturing each image sensor sheet of the multiple image sensor sheets to be modular with any other image sensor sheets of the multiple image sensor sheets;
the flexible substrate layer comprises polyethylene naphthalate or polyethylene terephthalate; or
the flexible substrate layer is optically transparent.

* * * * *